US006861407B2

(12) United States Patent
Carney

(10) Patent No.: US 6,861,407 B2
(45) Date of Patent: Mar. 1, 2005

(54) METHODS OF THERAPY WITH THROMBIN DERIVED PEPTIDES

(75) Inventor: Darrell H. Carney, Dickinson, TX (US)

(73) Assignee: The Board of Regents, The University of Texas System, Austin, TX (US)

( * ) Notice: Subject to any disclaimer, the term of this patent is extended or adjusted under 35 U.S.C. 154(b) by 199 days.

(21) Appl. No.: 10/050,611

(22) Filed: Jan. 16, 2002

(65) Prior Publication Data

US 2002/0187933 A1 Dec. 12, 2002

Related U.S. Application Data

(63) Continuation-in-part of application No. 09/904,090, filed on Jul. 12, 2001.
(60) Provisional application No. 60/217,583, filed on Jul. 12, 2000.

(51) Int. Cl.[7] .......................... A61K 38/36; A61K 38/17
(52) U.S. Cl. ........................... 514/13; 514/12; 530/326; 623/1.42
(58) Field of Search ..................... 514/12, 13; 530/326; 623/1.42

(56) References Cited

U.S. PATENT DOCUMENTS

| | | | |
|---|---|---|---|
| 5,352,664 A | 10/1994 | Carney et al. | 514/13 |
| 5,500,412 A | 3/1996 | Carney et al. | 514/13 |
| 6,033,436 A | 3/2000 | Steinke et al. | |
| 2002/0061852 A1 | 5/2002 | Carney | |

FOREIGN PATENT DOCUMENTS

| | | |
|---|---|---|
| WO | WO 88/03151 | 5/1988 |
| WO | WO 94/25056 | 11/1994 |
| WO | WO 99/53943 | 10/1999 |
| WO | WO 00/24412 | 5/2000 |
| WO | WO 02/04008 | 1/2002 |

OTHER PUBLICATIONS

Tsopanoglou, N.E., and Maragoudakis, M.E., "On the Mechanism of Thrombin–induced Angiogenesis," *J. Biol. Chem.*, 274(34):23969–23976 (1999).
Coleman, C.L., et al., "Systemic Injection of Thrombin Peptide TP508 Mitigates Angioplasty–related Restenosis in Hypercholesterolemic Rabbit Iliac Arteries," Abstract LB14, Presented at the Experimental Biology 2001 Meeting (Orlando, Florida).
Hendel, R.C., et al., "Effect of Intracoronary Recombinant Human Vascular Endothelial Growth Factor on Myocardial Perfusion," *Journal of The American Heart Association*, 101(2):118–121, (2000).
Aoki, M., et al., "Angiogenesis induced by hepatocyte growth factor in non–infarcted myocardium and infarcted myocardium: up–regulation of essential transcription factor for angiogenesis, ets," *Gene Therapy*, 7(5):417–427, (2000).

Pecher, P., and Schumacher, B.A., "Angiogenesis is Ischemic Human Myocardium: Clinical Results After 3 Years," *The Annals of Thoracic Surgery*, 69(5):1414–1419, (2000).
Kawasuji, M., et al., "Therapeutic Angiogenesis With Intramyocardial Administration of Basic Fibroblast Growth Factor," *The Annals of Thoracic Surgery*, 69(4):1155–1161, (2000).
Rosengart, T.K., et al., "Six–Month Assessment of a Phase I Trial of Angiogenic Gene Therapy for the Treatment of Coronary Artery Disease Using Direct Intramyocardial Administration of an Adenovirus Vector Expressing the VEGF121 cDNA," *Annals of Surgery*, 230(4):466–472, (1999).
Laham, R.J., et al., "Intracoronary and Intravenous Administration of Basic Fibroblast Growth Factor: Myocardial and Tissue Distribution," *Drug Metabolism and Disposition*, 27(7):821–826, (1999).
Sellke, F.W., et al., "Therapeutic Angiogenesis With Basic Fibroblast Growth Factor: Technique and Early Results," *The Annals of Thoracic Surgery*, 65(6):1540–1544, (1998).
Folkman, J., "Angiogenic Therapy of the Human Heart," *Journal of The American Heart Association*, 97(7):628–629, (1998).
McKenna, C.J., et al., "Selective $ET_A$ Receptor Antagonism Reduces Neointimal Hyperplasia in a Porcine Coronary Stent Model," *Journal of The American Heart Association*, 97(25):2551–2556, (1998).
Frimerman, A., et al., "Chimeric DNA–RNA Hammerhead Ribozyme to Proliferating Cell Nuclear Antigen Reduces Stent–Induced Stenosis in a Porcine Coronary Model," *Journal of The American Heart Association*, 99(5):697–703, (1999).
Voisard, R., et al., "High–dose diltiazem prevents migration and proliferation of vascular smooth muscle cells in various in–vitro models of human coronary restenosis," *Coronary Artery Disease*, 8(3/4):189–201, (1997).
Nadir, M., et al., "Inhibition of coronary restenosis by antithrombin III in atherosclerotic swine," *Coronary Artery Disease*, 7(11):851–861, (1996).
Munro, E., et al., "Inhibition of human vascular smooth muscle cell proliferation by lovastatin: the role of isoprenoid intermediates of cholesterol synthesis," *European Journal of Clinical Investigation*, 24(11):766–772, (1994).

(List continued on next page.)

*Primary Examiner*—Robert A. Wax
(74) *Attorney, Agent, or Firm*—Hamilton, Brook, Smith and Reynolds, P.C

(57) ABSTRACT

The present invention relates to a method for promoting cardiac tissue repair comprising administering to the cardiac tissue a therapeutically effective amount of an angiogenic thrombin derivative peptide and/or inhibiting or reducing vascular occlusion or restenosis. The invention also relates to methods of stimulating revascularization. In yet another embodiment, the invention relates to the use of thrombin derivative peptides in the manufacture of a medicament for the methods described herein.

13 Claims, 2 Drawing Sheets

OTHER PUBLICATIONS

Chen, S.J., et al., "Mithramycin Inhibits Myointimal Proliferation After Balloon Injury of the Rat Carotid Artery In Vivo," *Circulation,* 90(5):2468–2473, (1994).

Shi, Y., et al., "Downregulation of c–myc Expression by Antisense Oligonucleotides Inhibits Proliferation of Human Smooth Muscle Cells," *Circulation,* 88(3):1190–1195, (1993).

Speir, E., and Epstein, S.E., "Inhibition of Smooth Muscle Cell Proliferation by an Antisense Oligodeoxynucleotide Targeting the Messenger RNA Encoding Proliferating Cell Nuclear Antigen," *Circulation,* 86(2):538–547, (1992).

Stiernberg, J., et al., "The Role of Thrombin and Thrombin Receptor Activating Peptide (TRAP–508) in Initiation of Tissue Repair," *Thrombosis and Haemostasis,* 70(1):158–162, (1995).

Carney, D.H., et al., "Enhancement of Incisional Wound Healing and Neovascularization in Normal Rats by Thrombin and Synthetic Thrombin Receptor–activating Peptides," *J. Clin. Invest.,* 89:1469–1477, (1992).

Carney, D.H., et al., "Role of High–Affinity Thrombin Receptors in Postclotting Cellular Effects of Thrombin," *Seminars in Thrombosis and Hemostasis,* 18(1):91–102, (1992).

Stiernberg, J., et al., "Acceleration of full–thickness wound healing in normal rats by the synthetic thrombin peptide, TP508," *Wound Repair and Regeneration,* 8(3):204–215, (2000).

Glenn, K.C., et al., "Synthetic Peptides Bind to High–Affinity Thrombin Receptors and Modulate Thrombin Mitogenesis," *Peptide Research,* 1(2):65–73, (1988).

Sower, L.E., et al., "Thrombin Peptide, TP508, Induces Differential Gene Expression in Fibroblasts through a Non-proteolytic Activation Pathway," *Experimental Cell Research,* 247:422–431, (1999).

Carney, D.H., "Postclotting Cellular Effects of Thrombin Mediated by Interaction with High–Affinity Thrombin Receptors," *Thrombin: Structure and Function,* Chapter 10, pp. 351–396, (1992).

METHODS OF THERAPY WITH THROMBIN DERIVED PEPTIDES

RELATED APPLICATIONS

This application is a continuation-in-part of U.S. application Ser. No. 09/904,090, filed Jul. 12, 2001, which claims the benefit of U.S. Provisional Application Ser. No. 60/217,583, filed Jul. 12, 2000, the entire teachings of which are incorporated herein by reference.

GOVERNMENT SUPPORT

The invention was supported, in whole or in part, by a grant R43 HL64508 from National Institutes of Health. The Government has certain rights in the invention.

BACKGROUND OF THE INVENTION

Human alpha-thrombin appears to have growth-promoting activity for a wide variety of cells from various tissues. For example, alpha-thrombin has been shown to initiate proliferation of fibroblastic cells in culture without addition of serum or other purified growth factors, to synergize with epidermal growth factor in certain hamster fibroblasts and human endothelial cells, to initiate cell division or DNA synthesis in mammalian lens epithelial and spleen cells and actuate monocytes and neutrophils. Yet, the use of thrombin as a growth factor and its potential importance to wound healing has not been widely acclaimed. In part, this may be due to the complexity of thrombin's involvement with coagulation, platelet activation, and initiation of cell proliferation as well as to the complex regulation of thrombin and thrombin-like molecules by serum protease inhibitors and by cell-released protease nexins. This complexity and high degree of physiologic regulation, however, supports the potential importance of this initiation pathway in wound healing.

Thrombin may also play a role in both normal revascularization and migration of cells from the blood to the site of injury and the abnormal metastasis and angiogenesis associated with tumors. The ability of thrombin to increase endothelial cell proliferation and alter the barrier function of blood vessels may contribute to angiogenesis and inflammation at sites of tissue injury.

Thrombin derivative peptides have been described by the present inventors for the agonizing and antagonizing thrombin and/or thrombin receptor activity, such as in the treatment of wounds. U.S. Pat. No. 5,500,412 or 5,352,664, the contents of which are incorporated herein by reference in their entirety. However, the patent does not teach the novel use of the thrombin derivative peptides for the treatment of damaged cardiac tissue, for revascularization, or for inhibition of vascular occlusion and restenosis.

SUMMARY OF THE INVENTION

The invention relates to methods for promoting cardiac tissue or myocardium repair, promoting vascularization or inhibiting vascular occlusion or restenosis. The method comprises administering to the cardiac tissue or blood vessels a therapeutically effective amount of an angiogenic thrombin derivative peptide. In a preferred embodiment, the peptide is a peptide described in U.S. Pat. No. 5,500,412 or 5,352,664, the contents of which are incorporated herein by reference in their entirety. For example, the peptide can preferably comprises a thrombin receptor binding domain having the sequence Arg-Gly-Asp-Ala (SEQ ID NO: 1); and a serine esterase conserved sequence. Preferred serine esterase conserved sequences comprise Asp-Ala-Cys-Glu-Gly-Asp-Ser-Gly-Gly-Pro-Phe-Val (SEQ ID NO: 2). In yet a more preferred embodiment, the thrombin derivative peptide comprises the amino acid sequence: Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 3), such as a peptide which consists of the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 3). The peptide having the sequence of SEQ ID NO. 3 is also referred to herein as "TP508").

Alternatively, the thrombin derivative peptide is a physiologically functional equivalent of the thrombin derivative peptide comprising the amino acid sequence of SEQ ID NO: 3. In a particular embodiment, the thrombin derivative peptide comprises the modified amino acid sequence: Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-$NH_2$(SEQ ID NO: 4). In a particular embodiment, the thrombin derivative peptide consists of the modified amino acid sequence: Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-$NH_2$(SEQ ID NO: 4).

The peptide can preferably be administered during or following cardiac surgery, for example by direct or catheter-mediated injection into damaged or ischemic cardiac tissue as a soluble peptide or in a sustained release formulation.

The invention also relates to a method of stimulating revascularization or vascular endothelial cell proliferation comprising administering to cardiac tissue a therapeutically effective amount of an angiogenic thrombin derivative peptide, as described herein.

The invention also relates to a method of preventing vascular occlusion or restenosis comprising administering a therapeutically effective amount of the angiogenic thrombin receptor binding peptide to blood vessels, for example, by systemic injection, by delivering the peptides to sites of vascular injury by catheter, or by attachment of the peptide to stents.

DETAILED DESCRIPTION OF THE INVENTION

Figure 1:
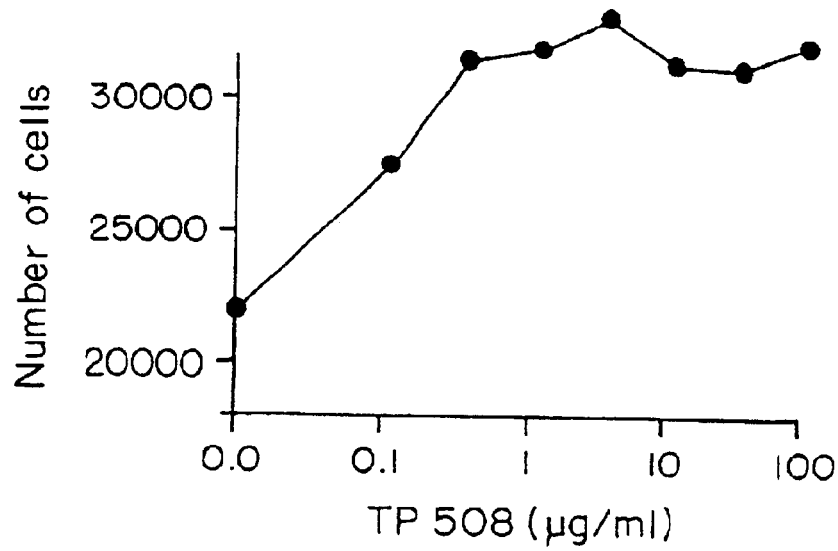
FIG. 1 is a graph showing that increasing concentrations of TP508 (peptide having the amino acid sequence of SEQ ID NO: 3) stimulates the proliferation of human microvascular endothelial cells in vitro. The graph shows the cell count 48 hours after being administered various concentrations of TP508 (indicated in $\mu$g/ml).

Cardiovascular diseases are generally characterized by an impaired supply of blood to the heart or other target organs. Myocardial infarction (MI) result from narrowed or blocked coronary arteries in the heart which starves the heart of needed nutrients and oxygen. When the supply of blood to the heart is compromised, cells respond by generating compounds that induce the growth of new blood vessels so as to increase the supply of blood to the heart. These new blood vessels are called collateral blood vessels. The process by which new blood vessels are induced to grow out of the existing vasculature is termed angiogenesis, and the substances that are produced by cells to induce angiogenesis are the angiogenic factors.

When heart muscle is deprived of oxygen and nutrients due to vascular occlusion, the heart muscle tissue becomes ischemic and looses its ability to contract and function. This loss of function may be restored by natural signals from the ischemic heart muscle that induce angiogenic revascularization through development of collateral vessels that bypass the occlusion. This revascularization or angiogenesis involves the stimulation of endothelial cell proliferation and migration and budding off of new blood vessels. In many cases, however, the natural signals are not sufficient to cause collateral vessel growth and the ischemic tissue can become fibrotic or necrotic. If this process is not reversed by procedures to open the occluded vessels or further induction of collateral blood vessels, the heart may become totally disfunctional and require transplantation.

The peptides described herein can be employed to induce angiogenic proliferation and migration of endothelial cells resulting in formation of new capillaries and collateral vessels to help restore function to damaged or ischemic heart tissue. These peptides may preferably be directly injected into or applied to heart tissue during open chest procedures for bypass surgery or insertion of ventricular assist devices or delivered by catheter injection into the heart as a soluble peptide or in a sustained release formulation.

Endothelial cell proliferation, such as that which occurs in angiogenesis, is also useful in preventing or inhibiting restenosis following balloon angioplasty. The balloon angioplasty procedure often injures the endothelial cells lining the inner walls of blood vessels and disrupts the integrity of the vessel wall. Smooth muscle cells and inflammatory cells often infiltrate into the injured blood vessels causing a secondary obstruction in a process known as restenosis. Stimulation of the proliferation and migration of the endothelial cells located at the periphery of the balloon-induced damaged area in order to cover the luminal surface of the vessel with a new monolayer of endothelial cells would potentially restore the original structure of the blood vessel.

Preferably, endothelialization comprises re-endothelialization after angioplasty, to reduce, inhibit or prevent restenosis. Those of skill in the art will recognize that patients treated according to the methods of the present invention may be treated with or without a stent.

An inflatable balloon catheter with peptide coating the balloon or a catheter that directly injects the peptide into the wall of the vessel may also be employed to deliver the substance to a targeted artery.

Balloon angioplasty is a common treatment of ischemic heart disease which involves the inflation of a balloon in a clogged blood vessel in order to open the blocked blood vessel. Unfortunately, this method of treatment results in injury to the endothelial cells lining the inner walls of blood vessels often leading to restenosis. The peptides described herein can be employed to induce proliferation and migration of the endothelial cells located at the periphery of the balloon induced damaged area in order to cover the luminal surface of the vessel with a new monolayer of endothelial cells, hoping to restore the original structure of the blood vessel. Coronary angioplasty is frequently accompanied by deployment of an intravascular stent to help maintain vessel function and avoid restenosis. Stents have been coated with heparin to prevent thrombosis until the new channel formed by the stent can endothelialize. The peptides described herein can be applied directly to the stent, using methods known to those of skill in the art. The peptides can be locally applied or systemically administered to enhance endothelialization of the vessel or vessel wall and/or to modulate other processes to inhibit or reduce thrombosis and restenosis.

The present invention preferably employs synthetic or naturally derived polypeptide agonists of thrombin receptor mediated events. Both of these classes of agents possess a thrombin receptor binding domain which includes a segment of the polypeptide that is capable of selectively binding to the high-affinity thrombin receptor. This segment of the polypeptide includes a sequence of amino acids homologous to a tripeptide cell binding domain of fibronectin.

In addition to the thrombin receptor binding domain, the stimulatory (agonistic) polypeptides possess a sequence of amino acids having sequences derived from the N-terminal amino acids of a dodecapeptide previously shown to be highly conserved among serine proteases. However, the inhibitory polypeptides do not include these serine esterase-conserved sequences.

For example, the invention provides a number of polypeptides useful in promoting cardiac tissue repair. For such applications, the invention provides a polypeptide derivative of thrombin (or a functional equivalent of such a derivative) which has a thrombin receptor binding domain as well as a domain with a serine esterase conserved sequence of at least 12 amino acids. The invention also provides a polypeptide compound of at least 23 L-amino acids which has both a thrombin receptor binding domain and a domain with a serine esterase conserved amino acid sequence.

In one embodiment, the invention provides for several polypeptides containing specific amino acid sequences, such as a polypeptide compound in which the thrombin receptor binding domain includes the L-amino acid sequence Arg-Gly-Asp-Ala (SEQ ID NO: 1) together with the serine esterase conserved amino acid sequence, Asp-Ala-Cys-Glu-Gly-Asp-Ser-Gly-Gly-Pro-Phe-Val (SEQ ID NO: 2). In a preferred embodiment, the polypeptide compound includes the L-amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 3). The polypeptide compound can be modified by amidation of the carboxy terminus. For example, SEQ ID NO: 3 can be amidated as follows: Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-$NH_2$ (SEQ ID NO: 4).

The invention also provides for a pharmaceutical composition for promoting tissue repair which includes a therapeutically effective concentration of any of the compounds described above combined with a pharmaceutically acceptable excipient. Typically, such compositions include, for example, sufficient concentrations of the polypeptides to effect a stimulatory action on the thrombin receptor as demonstrated herein. Thus, such compositions should typically include sufficient concentrations to obtain levels of the polypeptides at the target site which are shown in vitro to stimulate the receptor. When endogenous levels of a secondary signal are believed to be inadequate, compositions may be employed which further include the addition of a therapeutically effective concentration of VEGF, alpha-thrombin, gamma-thrombin or other growth factors. Such combinations may exert an additive or synergistic effect. In certain cases, if tissue damage is so extensive that cells capable of responding to the polypeptides are not present in sufficient quantities, it is expected that responsive cells could be co-injected to provide a therapeutically effective combination.

Suitable carriers also provide for release of the active ingredient and preferably for a slow, sustained release over time at the target site. A number of synthetic biodegradable polymers can serve as carriers with sustained release characteristics. Examples of these polymers include poly α-hydroxy esters such as polylactic acid/polyglycolic acid homopolymers and copolymers, polyphosphazenes (PPHOS), polyanhydrides and poly(propylene fumarates).

Polylactic acid/polyglycolic acid (PLGA) homo and copolymers are well known in the art as sustained release vehicles. The rate of release can be adjusted by the skilled artisan by variation of polylactic acid to polyglycolic acid ratio and the molecular weight of the polymer (see Anderson, et al., *Adv. Drug Deliv. Rev.* 28:5 (1997), the entire teachings of which are incorporated herein by reference). The incorporation of poly(ethylene glycol) into the polymer as a blend to form microparticle carriers allows further attenuation of the release profile of the active ingredient (see Cleek et al., *J. Control Release* 48:259 (1997), the entire teachings of which are incorporated herein by reference). PGLA microparticles are often mixed with pluronic gels or collagen to prevent aggregation and to make the microparticles suitable for direct injection.

PPHOS polymers contain alternating nitrogen and phosphorous with no carbon in the polymer backbone, as shown below in Structural Formula (1):

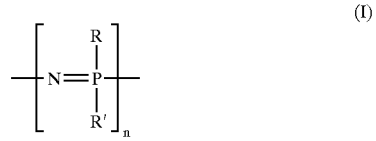

(I)

The properties of the polymer can be adjusted by suitable variation of side groups R and R' that are bonded to the polymer backbone. For example, the degradation of and drug release by PPHOS can be controlled by varying the amount of hydrolytically unstable side groups. With greater incorporation of either imidazolyl or ethylglycinato substituted PPHOS, for example, an increase in degradation rate is observed (see Laurencin et al., *J Biomed Mater. Res.* 27:963 (1993), the entire teachings of which are incorporated herein by reference), thereby increasing the rate of drug release.

Polyanhydrides, shown in Structural Formula (II), have well defined degradation and release characteristics that can be controlled by including varying amounts of hydrophobic or hydrophilic monomers such as sebacic acid and 1,3-bis (p-carboxyphenoxy)propane (see Leong et al., *J. Biomed. Mater. Res.* 19:941 (1985), the entire teachings of which are incorporated herein by reference).

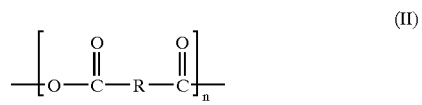

(II)

Poly(propylene fumarates) (PPF) are highly desirable biocompatible implantable carriers because they are an injectable, in situ polymerizable, biodegradable material. "Injectable" means that the material can be injected by syringe through a standard needle used for injecting pastes and gels. PPF, combined with a vinyl monomer (N-vinyl pyrrolidinone) and an initiator (benzoyl peroxide), forms an injectable solution that can be polymerized in situ (see Suggs et al., *Macromolecules* 30:4318 (1997), Peter et at., *J Biomater. Sci. Poly,. Ed.* 10:363 (1999) and Yaszemski et at., *Tissue Eng.* 1:41 (1995), the entire teachings of which are incorporated herein by reference).

As used herein, a therapeutically effective concentration is defined as a concentration of the particular agent which provides a satisfactory increase in the rate of repair or angiogenesis or which provides a satisfactory reduction or inhibition of restenosis or vascular occlusion. Again, such concentrations are believed to correspond to levels sufficient to elicit a stimulation of the high-affinity thrombin receptor in vitro. However, it is believed that the compositions will prove most effective when the stimulatory (agonistic) polypeptides are present at a concentration of from 0.1 $\mu$M to 10 $\mu$M.

For purposes of the present invention, a thrombin derivative is defined as any molecule with an amino acid sequence derived at least in part from that of thrombin, whether synthesized in vivo or in vitro. Accordingly, a thrombin derivative, as referred to herein, designates a polypeptide molecule which comprises fewer amino acids than thrombin.

A physiologically functional equivalent of a thrombin derivative encompasses molecules which differ from thrombin derivatives in particulars which do not affect the function of the thrombin receptor binding domain or the serine esterase conserved amino acid sequence. Such particulars may include, but are not limited to, conservative amino acid substitutions and modifications, for example, amidation of the carboxyl terminus, acetylation of the amino terminus, conjugation of the polypeptide to a physiologically inert carrier molecule, or sequence alterations in accordance with the serine esterase conserved sequences.

A thrombin receptor binding domain is defined as a polypeptide sequence which directly binds to the thrombin receptor and/or competitively inhibits binding between high-affinity thrombin receptors and alpha-thrombin.

A domain having a serine esterase conserved sequence comprises a polypeptide sequence containing at least 4–12 of the N-terminal amino acids of the dodecapeptide previously shown to be highly conserved among serine proteases (Asp-$X_1$-Cys-$X_2$-Gly-Asp-Ser-Gly-Gly-Pro-$X_3$-Val-SEQ ID NO: 5); wherein $X_1$ is either Ala or Ser; $X_2$ is either Glu or Gln; and $X_3$ is either Phe, Met, Leu, His, or Val).

A stimulatory polypeptide is defined as a polypeptide derivative of thrombin, or a physiologically functional equivalent thereof, having the ability to both bind to and stimulate the thrombin receptor. Therefore, the stimulatory peptides will include both a thrombin receptor binding domain and a domain with a serine esterase conserved amino acid sequence.

The invention is illustrated by the following examples, which are not intended to be limiting in any way.

EXEMPLIFICATION

Example 1

TP508 Stimulates the Proliferation and Migration of Human Endothelial Cells In Vitro To determine if TP508 could directly induce proliferation of endothelial cells, human microvascular endothelial cells were purchased from Clonetics, plated on tissue culture grade plastic in 24 well culture dishes and serum starved for 24 hours. Cells were stimulated in medium with or without TP508 for 48 hours, at which time proliferation was assessed using a direct cell count. As shown in FIG. 1, TP508 stimulated proliferation of microvascular endothelial cells by 30 to 50% over those treated in medium alone (1.0 µg/ml TP508). This effect appeared to be specific since the growth of smooth muscle cells isolated from rat aorta was not affected by TP508.

Figure 2:
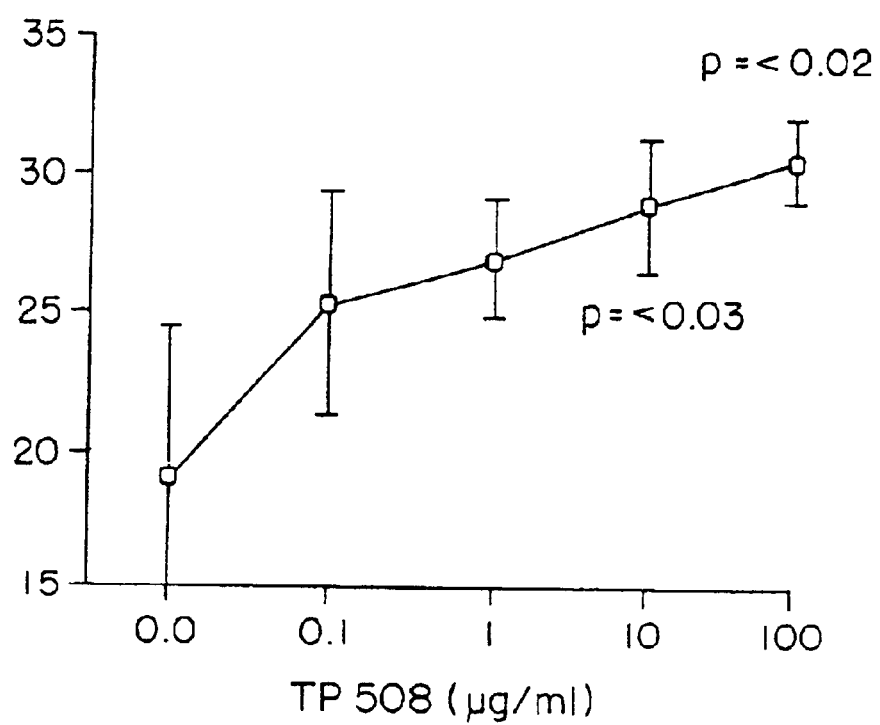
FIG. 2 is a graph showing that increasing concentrations of TP508 stimulates the migration of microvascular endothelial cells on plastic. The graph shows the distance migrated by the cells after being administered various concentrations of TP508 (indicated in $\mu$g/ml).
Figure 3:
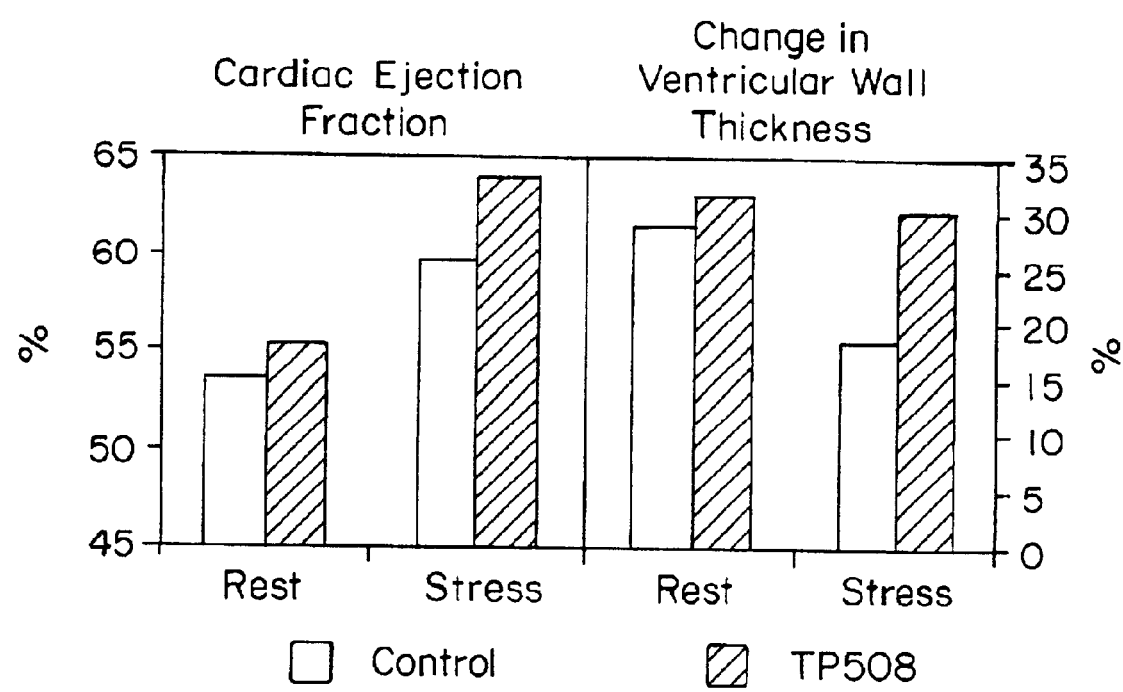
FIG. 3 is a graph showing changes in cardiac function in TP508 treated and control pigs in porcine model of cardiac ischemia.

TP508 effects on migration of human endothelial cells was assessed using an in vitro monolayer wound assay in which endothelial cells were plated in 35 mm culture dishes and allowed to grow to near confluency for three days, at which time the monolayer was "wounded" by scraping across the center of the dish with a rubber policeman to remove a band of cells. Photographs were taken at this point, and the cells were then treated with fresh medium alone or medium containing various concentrations of TP508 and allowed to grow for an additional 48 hours. The cells were re-photographed, and the distance that the endothelial cells migrated into the wounded area was measured. As shown in FIG. 2, TP508 stimulated migration of endothelial cells, even when the cells were cultured on plastic alone.

These studies demonstrated that TP508 has direct angiogenic effects on human endothelial cells causing increased proliferation and migration in vitro. Additional studies indicate that exposure of endothelial cells to TP508 has a protective effect to prevent death of cells caused by oxidative exposure. This protective effect may also contribute to processes of re-endothelialization and angiogenesis.

Example 2

TP508 Stimulates Angiogenesis In Vitro in a Chorioalloantoic Membrane Model

Studies with full dermal surgical incisions and open excisional wounds in the backs of rats showed that a single topical application of TP508 stimulates revascularization and the patency of blood vessels traversing a surgical incision. Two surgical incisional wounds were made on the back of a rat. One wound was treated with a single application of TP508 (0.1 µg); the other was untreated. Blood vessels were attracted to the treated wound rather than the control.

Addition of TP508 to agar disks placed on the chorioalloantoic membrane of chicken embryos resulted in an angiogenic outgrowth of blood vessels. Blood vessels were stimulated to grow into agar disks containing TP508. There was also an increase in collateral vessel outgrowth in vessels distal to the plug similar to that observed with other angiogenic factors.

Example 3

TP508 Showed Efficacy in Treating Myocardial Ischemia in a Porcine Model.

Yucatan minipigs had toroid shaped ameroid occluders placed on their proximal left circumflex arteries. The ameroid imbibed water over time, causing constriction of the vessel. Occlusion was verified four weeks after surgery by contrast enhanced angiography. At that time, each animal's chest was reopened, whereupon the region of ischemia was injected with a slow release formulation of TP508, i.e., TP508-containing PGLA microspheres, suspended in a Pluronic gel. The PLGA microspheres, which were prepared as described in Example 6, gave an initial burst release of drug (50% of load in 24 hours) and then displayed controlled release for another 3–4 days, by which time 80% of the load had been released. The gel used was 30% w/v Pluronic F68 in 0.9% saline. To each milliliter of gel, on ice to reduce the viscosity, 3.3 mg of PLGA microspheres were added immediately before injection. This gave a TP508 dose of 100 µg/ml of gel, which was injected into ten sites (100 µl per site) in the ischemic area. Controls received PLGA microspheres in Pluronic gel without TP508. Baseline, and post-treatment angiograms and echocardiograms were obtained.

Indices for myocardial wall thickening and cardiac ejection fraction showed trends that TP508 treated animals tolerated dobutamine-induced stress better than controls. After three weeks, the animals were evaluated with contrast enhanced echocardiography. Initial results on this limited number of animals demonstrated that TP508 treated animals under dobutamine stress had a slightly larger increase in ejection fraction and better maintained wall thickening compared to controls. Thus, this treatment appears to help restore functionality to the ischemic heart muscle.

Example 4

TP508 Stimulates Myocardial Revascularization in a Rabbit Model

TP508, formulated in sustained release PLGA microspheres, was injected into ischemic rabbit myocardium. An ameroid occluder was placed over the lateral division of the left main coronary artery of two rabbits just inferior to the A-V groove, as described in Operschall et al., J. Appl. Physiol. 88:1438 (2000). Two weeks after placement, the animals' chests were reopened. In one animal, TP508 microspheres in pluronic gel (as described in Example 3) were injected into eight discrete locations within, and around, the area served by the occluded vessel. The other animal served as an untreated control. Approximately four weeks post-injection, the animals were sacrificed and their hearts fixed in 10% buffered formalin for 24 hours. Hearts were then sectioned across the area of interest and stained by hematoxylin-eosin and immunolabelled against Von Willebrand Factor (vWF), an endothelial cell marker.

Histology demonstrated that the control animal had significant fibrosis in the area served by the occluder. The TP508 treated heart, on the other hand, had healthy appearing myocardium with a larger number of functional capillaries with obvious red blood cells.

Example 5

TP508 Suppresses Restenosis in a Hypercholesterolemic Rabbit Model

This procedure was designed to provide a system for testing the efficacy of a Test Sample to inhibit neointimal formation and vascular occlusion following angioplasty in hypercholesterolemic New Zealand White Rabbits. The animals were fed a high fat diet consisting of 0.5% cholesterol and 2.0% peanut oil for 3 weeks. The animals were pretreated 24 hours prior to surgery; the iliac artery was injured with balloon angioplasty as described; and the animals were are treated with TP-508 for 7 days. The animals were maintained on a high fat diet for 4 weeks. Angiography was conducted prior to balloon angioplasty and at termination of the experiment. The injured and uninjured iliac arteries were harvested and prepared for histology. Morphometric measurements were made of the lumen, the neointima (if present), and the tunica media.

Test samples of TP-508 were dissolved/diluted in a sterile, pyrogen-free saline to the desired concentration and administered by intravenous injection in a 0.2 ml volume one day prior to surgery, the day of surgery, and for 6 successive days post surgery.

A 5 cm midline neck incision was made and the right carotid was exposed, proximately ligated, and incised. A 4 Fr Berman Balloon Angiographic Catheter was then introduced into the aorta. A 5 Fr sheath was introduced into the aorta via the 4 Fr Berman Balloon Angiographic Catheter. Three ml of blood was collected for cholesterol count. The rabbit was then injected with heparin and more anesthetics (if necessary). To visualize the iliac arteries, 6 ml of Hypaque 76% mixed with 4 ml sterile saline was injected through the catheter. Imaging was acquired of the iliac arteries (image is marked with grid and scissors are placed on the right side). The 4 Fr Berman Balloon Angiographic Catheter was removed from the sheath. A 0.014"/3.0 mm×20.0 mm/120 cm Balloon Catheter was then inserted through the sheath into the aorta and to the iliac artery. The balloon was inflated 3 times at 10 ATM for 30 seconds with 1 minute intervals. The catheter and sheath were then removed. The right carotid artery was ligated with 3.0 silk sutures. The neck incision was closed with PDS and the skin stapled and dressed with double antibiotic ointment.

The test sample(s) or control sample(s) were then administered to the rabbit. The Test Sample was diluted in the following manner: 0.3 ml of saline was drawn into a 1.0 ml syringe with a 23 G 1" needle. The volume was injected into the TP-508 vile. After the TP-508 dissolved, 0.25 ml of the solution was removed and administered. The cannulation tube was then flushed with saline. If the rabbit was a control, 0.2 ml of saline was injected and flushed with additional saline. The rabbit also received 0.3 ml of Buprenorphine via subcutaneous injection.

After surgery, the rabbit was allowed time to become alert while resting on the heating pad. The rabbit was then returned to his cage and allowed food and water ad libitum. The rabbits were maintained on the diet for 4 additional weeks until sacrifice.

Four weeks post-procedure, both iliac arteries were fixed in situ, harvested and prepared for histology. Digital images were then captured of the serial histological sections spaced approximately one millimeter apart and morphometric measurements were made of the lumen, the neointima (if present) and the tunica media throughout the region of injury.

Histology Summary

Morphohistological analysis of 19 samples were completed using Image-Pro Plus and Excel software. Of the 19 samples, 2 demonstrated compromise of the external elastic laming One sample of the 19 appeared to require additional sectioning. Therefore, 16 samples were compared comprising 7 treated and 9 saline controls.

The thickness of the restenotic lesion was determined by measuring the area of the neointima via digital analysis. The tunica media of the vessels was measured similarly. These values were then normalized by summing the area of these two regions and dividing that result by the area of a normal (un-injured) media found within the same histological slide series. It was verified that there was no significant difference between groups in the areas found for the uninjured media.

When comparing treated animals against controls, the extent of restenosis was analyzed via three distinct methods: the "single worst value" method, the "average lesion thickness" method, and the "average of all sections" method. The "single worst value" method compares the maximum restenosis value obtained between operated vessels. The "average lesion thickness" method compares the averages all abnormal points within a well-defined region of injury between operated vessels. Lastly, the "average of all sections" method compares the average thickness of all samples measured, regardless of whether or not they appeared to be part of the lesion. The means of these results were tested for statistical significance via the Student's T-test.

Data Summary

All data analysis was completed using the two-tailed t-test assuming unequal variances. Alpha is 0.05 and the mean difference is assumed to be 0. Each analysis includes n=7 for treated and n=9 for saline control. The results are summarized in the following Table 1. The "difference" value shown relates to the percentage change of the treated as compared to the corresponding control. Values noted with an asterix were statistically significant.

TABLE 1

| Technique: | Single Worst Value | | | Average Lesion Thickness | | | Average of All Sections | | |
| --- | --- | --- | --- | --- | --- | --- | --- | --- | --- |
| Measured Area: | Treated | Controls | Diff. | Treated | Controls | Diff. | Treated | Controls | Diff. |
| Neointima | .202 | .332 | −39%* | .158 | .245 | −36% | .117 | .185 | −37%* |
| Media | .113 | .133 | −15% | .123 | .152 | −19% | .116 | .140 | −17% |
| Neo + Media/Uninjured Media | 4.56 | 7.73 | −41%* | 4.18 | 5.87 | −29%* | 3.49 | 5.55 | −37%* |

CONCLUSION

The data shows that TP-508 significantly suppressed restenosis and vascular occlusion in the hypercholesterolemic rabbit model. This result is robust in that it is independent of the technique chosen for quantifying the results.

Example 6

Preparation of Polylactic Acid/Polyglycolic Acid Copolymer Microspheres of TP508

A double emulsion technique was used to prepare microspheres of polylactic acid/polyglycolic acid copolymer (PLA/PGA) containing TP508. Briefly, the matrix components were dissolved in methylene chloride and TP508 was dissolved in water. The two were gradually mixed together while vortexing to form a water-in-oil (W/O) emulsion. Polyvinyl alcohol (0.3% in water) was added to the emulsion with further vortexing to form the second emulsion (O/W), thereby forming a double emulsion: an O/W emulsion comprised of PLA/PGA droplets, and within those droplets, a second disperse phase consisting of TP508 in water. Upon phase separation, the PLA/PGA droplets formed discrete microspheres containing cavities holding TP508. To cause phase separation of the microspheres, a 2% isopropyl alcohol solution was added. The particles were collected by centrifugation, and then lyophilized to remove residual moisture. The composition of the matrix was varied to form microspheres with different release kinetics (Table 2).

TABLE 2

Composition of different microsphere formulations

| Formulation | PLA:PGA | Polymer M. Wt. | % TP508 | % poly-ethylene glycol |
|---|---|---|---|---|
| A | 50:50 | 46,700 | 5 | 0 |
| B | 50:50 | 7,200 | 5 | 0 |
| C | 50:50 | 46,700 | 5 | 5 |
| D | 50:50 | 46,700 | 5 | 0 |
| E | 75:25 | 120,000 | 5 | 0 |

The mean diameter of the microspheres was measured in a Coulter counter and the drug entrapment efficiency was measured by spectrophotometric assay at 276 nm following dissolution of a weighed sample of microspheres in methylene chloride and extraction of the released drug into water (Table 3).

TABLE 3

Formulation diameter and drug entrapment efficiency

| Formulation | Diameter, $\mu$m | TP508 Entrapment, % |
|---|---|---|
| A | 26.0 | 53.8 |
| B | 16.2 | 27.1 |
| C | 17.6 | 58.9 |
| D | 23.9 | 42.6 |
| E | 25.8 | 36.2 |

To measure TP508 release from the different PLA/PGA matrices, 20 mg of microspheres were placed in 1.0 ml of PBS contained in 1.5 ml polypropylene microcentrifuge tubes. Tubes were incubated at 37° C. and shaken at 60 rpm. At various times, the tubes were centrifuged and the supernatant containing released TP508 was removed and frozen for subsequent analysis. Fresh PBS was added to the microspheres and incubation was continued. TP508 in the supernatant was measured by absorbance at 276 nm. For each formulation, quadruplicate release determinations were performed. Formulations B and D showed no detectable drug release during 28 days of incubation at 37° C. The remaining formulations all released detectable amounts of TP508, although in all cases the amount of drug released fell below detectable limits (<1 $\mu$g/mg matrix/day) within 3–4 days. Formulations A and C showed the greatest release of TP508, releasing 60–80% of the entrapped drug over 3–4 days. The formulation with the fastest release kinetics, C, was chosen for further testing in in vivo studies described in Example 3 and Example 4.

While this invention has been particularly shown and described with references to preferred embodiments thereof, it will be understood by those skilled in the art that various changes in form and details may be made therein without departing from the scope of the invention encompassed by the appended claims.

---

What is claimed is:

1. A method for promoting cardiac tissue repair comprising administering to the cardiac tissue a therapeutically effective amount of the peptide Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-NH₂ (SEQ ID NO: 4).

2. The method of claim 1 wherein the peptide is administered during or following cardiac surgery.

3. The method of claim 1 wherein the peptide is administered by injection into the cardiac tissue.

4. The method of claim 1 wherein a sustained release formulation comprising the peptide is administered to the cardiac tissue.

5. The method of claim 4 wherein the sustained release formulation is a polylactic acid/polyglycolic acid microparticles comprising the peptide.

6. A method of stimulating revascularization of cardiac tissue comprising administering to cardiac tissue comprising administering to the cardiac tissue a therapeutically effective amount of the peptide Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-NH₂ (SEQ ID NO: 4).

7. A method of inhibiting restenosis in a patient following balloon angioplasty, said method comprising administering to the patient a therapeutically effective amount of the peptide Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-NH₂ (SEQ ID NO: 4).

8. The method of claim 7 wherein the peptide is coated onto a balloon angioplasty catheter.

9. The method of claim 7 wherein the peptide is administered systemically.

10. The method of claim 7 wherein the peptide is administered locally to a balloon induced damaged area of a blood vessel.

11. The method of claim 7 wherein a stent coated with the peptide is inserted into a blood vessel at a balloon induced damaged area.

12. A stent coated with the peptide Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-NH$_2$ (SEQ ID NO: 4).

13. A method of inhibiting vascular occlusion in a patient, said method comprising administering to the patient a therapeutically effective amount of the peptide Ala-Gly-Tyr-Lys-Pro-Asp-Glu-Gly-Lys-Arg-Gly-Asp-Ala-CysGlu-Gly-Asp-Ser-Gly-Gly-Pro-Phe-Val-NH$_2$ (SEQ ID NO: 4).

* * * * *

UNITED STATES PATENT AND TRADEMARK OFFICE
CERTIFICATE OF CORRECTION

PATENT NO. : 6,861,407 B2
DATED : March 1, 2005
INVENTOR(S) : Darrell H. Carney

It is certified that error appears in the above-identified patent and that said Letters Patent is hereby corrected as shown below:

Column 13,
Line 66, delete "comprising administering to cardiac tissue".

Column 16,
Lines 1-3, delete "Ala-Gly-Tyr-Lys-Pro-Asp-Glu-Gly-Lys-Arg-Gly-Asp-Ala-CysGlu-Gly-Asp-Ser-Gly-Gly-Pro-Phe-Val-$NH_2$" and substitute therefor: -- Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-$NH_2$ --.

Signed and Sealed this

Thirty-first Day of May, 2005

JON W. DUDAS
*Director of the United States Patent and Trademark Office*

SEQUENCE LISTING

<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: human fragment of thrombin

<400> SEQUENCE: 1

Arg Gly Asp Ala
 1

<210> SEQ ID NO 2
<211> LENGTH: 12
<212> TYPE: PRT
<213> ORGANISM: Artificial Sequence
<220> FEATURE:
<223> OTHER INFORMATION: human fragment of thrombin

<400> SEQUENCE: 2

Asp Ala Cys Glu Gly Asp Ser Gly Gly Pro Phe Val
 1               5                  10

<210> SEQ ID NO 3
<211> LENGTH: 23
<212> TYPE: PRT
<213> ORGANISM: Artificial Sequence -continued

```
<220> FEATURE:
<223> OTHER INFORMATION: human fragment of thrombin

<400> SEQUENCE: 3

Ala Gly Tyr Lys Pro Asp Glu Gly Lys Arg Gly Asp Ala Cys Glu Gly
1               5                   10                  15

Asp Ser Gly Gly Pro Phe Val
            20

<210> SEQ ID NO 4
<211> LENGTH: 23
<212> TYPE: PRT
<213> ORGANISM: Artificial Sequence
<220> FEATURE:
<223> OTHER INFORMATION: C-terminal amidated fragment of human thrombin
<220> FEATURE:
<221> NAME/KEY: AMIDATION
<222> LOCATION: 23
<223> OTHER INFORMATION: valine is amidated as CONH2

<400> SEQUENCE: 4

Ala Gly Tyr Lys Pro Asp Glu Gly Lys Arg Gly Asp Ala Cys Glu Gly
1               5                   10                  15

Asp Ser Gly Gly Pro Phe Val
            20

<210> SEQ ID NO 5
<211> LENGTH: 12
<213> ORGANISM: Artificial Sequence
<220> FEATURE:
<223> OTHER INFORMATION: human fragment of thrombin
<220> FEATURE:
<221> NAME/KEY: VARIANT
<222> LOCATION: 2
<223> OTHER INFORMATION: Xaa = Ala or Ser
<220> FEATURE:
<221> NAME/KEY: VARIANT
<222> LOCATION: 4
<223> OTHER INFORMATION: Xaa = Glu or Gln
<220> FEATURE:
<221> NAME/KEY: VARIANT
<222> LOCATION: 11
<223> OTHER INFORMATION: Xaa = Phe, Met, Leu, His or Val

<400> SEQUENCE: 5

Asp Xaa Cys Xaa Gly Asp Ser Gly Gly Pro Xaa Val
1               5                   10
```